United States Patent [19]

Zimmer et al.

[11] Patent Number: 4,465,786

[45] Date of Patent: Aug. 14, 1984

[54] CATALYST COMPOSITION FOR THE PREPARATION OF 3,3,3-TRIFLUOROPROPENE

[75] Inventors: Mark F. Zimmer, Clifton Park; William E. Smith, Schenectady; Donald F. Malpass, Jr., Waterford, all of N.Y.

[73] Assignee: General Electric Company, Waterford, N.Y.

[21] Appl. No.: 424,267

[22] Filed: Sep. 27, 1982

[51] Int. Cl.$^3$ ............................................. B01J 27/12
[52] U.S. Cl. ................................... 502/169; 502/228; 570/136
[58] Field of Search .................. 252/441, 442, 429 R; 502/169, 228

[56] References Cited

U.S. PATENT DOCUMENTS

| | | | |
|---|---|---|---|
| 2,745,886 | 5/1956 | Ruh et al. | 260/653 |
| 2,889,379 | 6/1959 | Ruh et al. | 260/653.4 |
| 3,385,794 | 5/1968 | Scherer et al. | 252/441 X |
| 3,651,156 | 3/1972 | Scherer et al. | 252/441 X |
| 3,855,151 | 12/1974 | Schindel | 252/441 X |
| 3,859,424 | 1/1975 | Scherer et al. | 252/441 X |
| 4,029,629 | 6/1977 | Jeram | 260/375 B |

FOREIGN PATENT DOCUMENTS 36-16715 11/1961 Japan.
49-133308 12/1974 Japan.

OTHER PUBLICATIONS

Industrial and Engineering Chemistry, vol. 52, No. 9, (Sep. 1960), pp. 783–784.

*Primary Examiner*—Patrick Garvin
*Attorney, Agent, or Firm*—Hedman, Gibson, Costigan & Hoare

[57] ABSTRACT

A catalyst composition useful in preparing 3,3,3-trifluoropropene by the reaction of hydrogen fluoride gas with a halogenated hydrocarbon is provided. A novel catalyst is prepared by simultaneous fluorination of chromium and aluminum oxides. This or conventional chromium oxyfluoride compounds may additionally be activated by contact with chlorine or pentachloroethane. A process for the preparation of 3,3,3-trifluoropropene is also contemplated.

8 Claims, No Drawings

CATALYST COMPOSITION FOR THE PREPARATION OF 3,3,3-TRIFLUOROPROPENE

This invention relates to the production of 3,3,3-trifluoropropene. More particularly, it relates to compositions which catalyze the reaction of halogenated hydrocarbons with hydrogen fluoride gas to produce 3,3,3-trifluoropropene.

BACKGROUND OF THE INVENTION

Fluorosilicone rubbers have become important synthetic rubber products because of their temperature stability and high resistance to solvents such as jet fuel. The fluorosilicone gums which can be vulcanized to form fluorosilicone rubber compounds are typically fluoroalkyl-substituted diorganopolysiloxanes such as those disclosed in U.S. Pat. No. 4,029,629 (Jeram) and commonly assigned copending U.S. application Ser. No. 253,282, filed Apr. 9, 1981 and now abandoned.

The fluoroalkyl-substituted diorganopolysiloxanes are most advantageously formed by hydrolysis of cyclic polysiloxane monomers such as 1,3,5-tris(3,3,3-trifluoropropyl)-1,3,5-trimethylcyclotrisiloxane (or "cyclic trimer"); and the cyclic trimer is advantageously prepared from 3,3,3-trifluoropropene and halogenated silanes via reactions described by Pierce et al., *Industrial and Engineering Chemistry*, Vol. 52, No. 9 (Sept. 1960), pp. 783–4, and illustrated as follows:

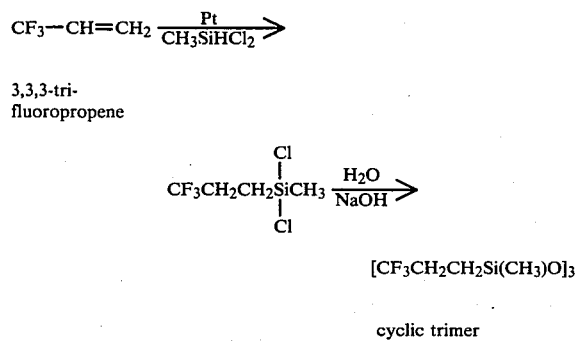

3,3,3-trifluoropropene cyclic trimer 3,3,3-trifluoropropene, therefore, can be seen to be an extremely important raw material in the production of fluorosilicone rubber. It is most commonly prepared by vapor-phase fluorination of halogenated hydrocarbons by exposure to hydrogen fluoride at elevated temperatures in the presence of a solid chromium oxyfluoride catalyst. Both the fluorination reaction and conventional chromium oxyfluoride catalysts are described in U.S. Pat. No. 2,745,886 (Ruh et al., 1956), U.S. Pat. No. 2,889,379 (Ruh et al., 1959) and Japan S.36 (1961)-16715 (Ruh et al., 1961), incorporated herein by reference.

Although the conventional chromium oxyfluoride catalysts widely used at the present time give extremely high reaction rates and yields initially, they are quickly deactivated by the formation of a carbonous deposit on the catalyst surface. The rate of deactivation is so rapid that economic operation of the fluorination process on an industrial scale is very difficult. All reported attempts to extend the life of chromium oxyfluoride catalysts by changing their composition or form have met with little success.

Extending the life of the catalysts by modifying process conditions has also been attempted, but these changes, while slightly prolonging catalyst life also result in decreased reaction rate, lower yield and disadvantageous process economics. For example, increasing the feed ratio of hydrogen fluoride to organic material slightly increases catalyst life but also increases the amount of unreacted hydrogen fluoride which must be recycled. Similarly, decreasing the reaction temperature tends to slow the deactivation of the catalyst but also decreases the reaction rate.

Various investigators and manufacturers of 3,3,3-trifluoropropene have noted that the presence of chlorinated organic compounds in the reaction can have a marked effect on the life of the chromium oxyfluoride catalyst. In particular, as described in Japan Kokai S.49 (1974)-133308 (Wada), the presence of either 1,1-dichloroethane or hexachloroethane in the reaction feed causes a lengthening in the catalyst life (defined by Wada as the time required for the yield to drop to 75 percent) of the chromium oxyfluoride. Several other chemically similar chlorinated or fluorinated compounds showed no such effect.

Using hexachloroethane with a chromium oxyfluoride catalyst results in a large improvement in catalyst life, but industrial use is hampered because of its physical properties. Hexachloroethane is a hard, semi-crystalline substance which sublimes at 187° C. and which is essentially insoluble in hydrogen fluoride and only partially soluble in the halogenated hydrocarbons commonly used to produce 3,3,3-trifluoropropene, for example 1,1,1,3-tetrachloropropane. Since only a fraction of the hexachloroethane introduced to the reaction is converted to a volatile product, the remaining hexachloroethane precipitates (in the absence of any material in which it is soluble) as the gases exiting the reaction chamber are cooled, causing clogging of processing lines and other difficulties.

Consequently, there is a need for a catalyst composition which will promote vapor-phase fluorination of halohydrocarbons, which has a long catalyst life, but which will be readily adaptable to industrial scale processing.

All of the patents and the application mentioned above are hereby incorporated by reference.

It has now been discovered that significant improvements in the life of chromium oxyfluoride catalysts can be achieved by a novel method for their preparation and/or employing, as part of the catalyst composition, chlorine or pentachloroethane to activate the chromium oxyfluoride.

SUMMARY OF THE INVENTION

Accordingly, it is the object of the present invention to provide a catalyst composition to promote the vapor-phase fluorination of halohydrocarbons by reaction with hydrogen fluoride gas having a long catalyst life.

It is a further object of the present invention to provide a catalyst composition useful in the production of 3,3,3-trifluoropropene which is compatible with common raw materials and products of said production so as not to require special separation techniques or other processing changes.

It is a further object of the present invention to provide a means of increasing the yield of 3,3,3-trifluoropropene from known fluorination reactions.

These and other objects are accomplished herein by a catalyst composition for promoting fluorination of halogenated hydrocarbons by vapor-phase reaction with hydrogen fluoride comprising a chromium oxyfluoride compound activated by contact with chlorine gas or pentachloroethane.

Another feature of the present invention includes an improved chromium oxyfluoride catalyst prepared from oxide starting materials by simultaneous fluorination.

Also contemplated herein are a novel method for the production of 3,3,3-trifluoropropene and a process for preparing a chromium oxyfluoride catalyst composition.

DETAILED DESCRIPTION OF THE INVENTION

The catalyst compositions of the present invention are prepared by contacting conventional chromium oxyfluoride catalysts with chlorine or pentachloroethane (pentalin), or by preparing an improved chromium oxyfluoride compound by a novel method involving the simultaneous fluorination of oxide starting materials. This improved chromium oxyfluoride catalyst may also be further enhanced by contact with chlorine or pentachloroethane.

Conventional chromium oxyfluoride catalysts, i.e., prepared according to the aforementioned Ruh et al. (1956) patent, may be prepared in a number of disclosed formulations, all of which entail heating a hydrated chromium fluoride, for example $CrF_3 \cdot 3H_2$, to a temperature of 350°–750° C. in the presence of oxygen. This "activation" of the chromium fluoride may be accomplished by contact with oxygen gas, an oxygen-containing gas (e.g., air) or a compound which liberates oxygen under activation conditions (e.g., $CrO_3$). Later Ruh et al. patents (1959 and 1961) disclose a slightly different catalyst composition also containing aluminum fluoride to prolong the catalyst life. This is currently the most commonly used catalyst for large scale manufacture of 3,3,3-trifluoropropene.

In contrast, the chromium oxyfluoride catalyst contemplated as a feature of the present invention is prepared by simultaneous fluorination of chromium trioxide and aluminum oxide. It is found that this yields a more intimate mixture of the salts which increases the activity and life of the catalyst.

By way of illustration, the aforementioned simultaneous fluorination may be carried out by first admixing the oxides, chromium trioxide and aluminum oxide (alumina), then adding the solids very slowly to hydrofluoric acid.

A sufficient amount of oxidizable organic material should be included in the admixture to reduce substantially all of the chromium to the trivalent state, substances such as formaldehyde, sucrose, toluene, polyethylene, xylene and the like being suitable for this purpose.

A strongly exothermic reaction results and the reaction is most advantageously kept cooled to below about 40° C. in order to minimize generation of hydrogen fluoride gas. The resulting slurry may be dried, then ground, or mixed with binders such as graphite and tableted, and finally oxidized at 350°–750° C.

The life and activity of the above chromium oxyfluoride catalyst, or of chromium oxyfluoride catalysts prepared conventionally, may be further enhanced as contemplated herein by employing chlorine or pentachloroethane in the fluorination reaction to activate and prolong the effectiveness of the chromium oxyfluoride compound.

Introduction of chlorine gas continuously along with the reactor feed (hydrogen fluoride gas plus halohydrocarbon to be fluorinated) in small amounts such as, for example 0.1 to 5.0 percent (preferably about 1.0–2.5%) of the feed mixture, results in dramatic reduction in deterioration of 3,3,3-trifluoropropene yield and deterioration of catalyst activity, to a point where the fluorination may be carried out indefinitely without need to regenerate or replace the catalyst.

While not so effective in prolonging catalyst life as chlorine, the introduction of pentachloroethane to the fluorination reaction in small amounts, such as, for example, 1 to 10 percent (preferably about 5.0%) of the reaction feed overcomes the disadvantages of employing hexachloroethane as a catalyst promoter. Pentachloroethane is a liquid at room temperature and is miscible with most chlorinated hydrocarbons, including tetrachloropropane, the most commonly used halohydrocarbon in 3,3,3-trifluoropropene preparation. Pentachloroethane also has a boiling point (161° C.) near that of 1,1,1,3-tetrachloropropane, which facilitates the recovery and recycling of pentachloroethane along with unreacted 1,1,1,3-tetrachloroethane, if necessary.

Use of pentachloroethane to activate the chromium oxyfluoride catalyst not only avoids the processing disadvantages associated with using hexachloroethane but results in a catalyst giving increased yield of trifluoropropene. While the working Example 4 (infra) shows that the small scale performance of hexachloroethane-promoted catalysts is superior to catalysts activated by pentachloroethane, the latter show marked improvement over unpromoted catalysts and offer large scale processing advantages which distinguish them over hexachloroethane-promoted catalysts.

The chlorine or pentachloroethane may be introduced separately to the fluorination reaction or along with the feed, and will have a beneficial effect whenever introduced. Best results, however, in terms of convenient operation and efficiency, are achieved if the chlorine or pentachloroethane are introduced continuously as part of the feed mixture, which allows simplification of the reaction apparatus and maximum control over the relative proportions of feed materials, as well as assuring continuous presence of the chlorine or pentachloroethane while the reaction is proceeding.

The amount of chlorine or pentachloroethane employed to contact the crhromium oxyfluoride compound is not critical so long as the desired enhancement effect is achieved. As with any catalyst, or catalyst component, the smallest amount producing the desired results is sought. As indicated above for illustration, however, it has been found that best results for fluorination of 1,1,1,3-tetrachloropropane are achieved with levels of chlorine around 1.0–2.5 percent of the feed mixture or levels of pentachloroethane around 5.0 percent of the feed mixture. Simple experimentation to arrive at an optimal mixture for the particular halohydrocarbon used, production equipment available and reaction conditions desired is contemplated.

In carrying out the fluorination of halohydrocarbons according to the invention using the new catalyst herein, the halohydrocarbon is vaporized and passed together with hydrogen fluoride (and chlorine or pentachloroethane) through a heated bed of the catalyst at a reaction temperature in the range of from about 125° C. to 600° C. Ordinarily, however, reaction temperatures in the range of 150° C. to 500° C. are employed, with temperatures below 350° C. to 400° C. being preferred for fluorinating most halohydrocarbons. The fluorination temperature is dependent not only upon the reactivity of halohydrocarbon which is to be reacted with hydrogen fluoride, but also upon the contact time, and other factors. The optimum temperature of fluorination also varies with the activity of the catalyst, which in turn depends partly upon its method of preparation and partly on whether chlorine or pentachloroethane is used.

The ratio of hydrogen fluoride to halohydrocarbon ("feed ratio") of the fluorination reaction may be varied within wide limits. Ordinarly, from 1–15 moles of hydrogen fluoride are employed per mole of the organic reactant. The preferred feed ratio herein is from about 6–12.

Contact time does not have a significant effect on the fluorination reaction, but contact times above about 0.1 second are generally employed to ensure maximum conversion of the starting material and minimization of recycling. Contact times longer than 20 seconds are ordinarily undesirable simply because of low throughput.

The halogenated hydrocarbons suitable as starting materials for the process of the present invention are saturated or unsaturated halohydrocarbons, containing 3 carbons and from 3 to 4 halogen atoms other than iodine, with one terminal carbon atom free of hydrogen. Such starting materials include, for example, 3,3,3-trichlorpropene, 3,3,3-tribromopropene, 3,3-dichloro-3-bromopropene, 1,1,1,3-tetrachloropropane, 1,1,1,3-tetrabromopropane, 3,3-dichloro-3-fluoropropene, 3,3-dibromo-3-fluoropropene, 3-bromo-3,3-difluoropropene, 3-chloro-3,3-difluoropropene, 1,1,3-trichloropropene, 1,1-dichloro-3-bromopropene, 1,3-dichloro-1,1-difluoropropane, 1,1,1-trichloro-3-bromopropane, etc. 1,1,1,3-tetrachloropropane is preferred.

The following working examples will further illustrate the practice of the present invention as herein disclosed. They are given by way of illustration and are not to be construed as limiting the invention.

EXAMPLE 1

A catalyst formulation prepared in accord with the present invention was prepared as follows:

1814.9 parts by weight of 52% aqueous hydrofluoric acid were added to a reaction vessel. In a separate container 1148 parts by weight of chromium trioxide were mixed with 163.1 parts by weight of aluminum oxide (alumina) and 348.9 parts by weight of sugar (sucrose). This mixture of solids was then added extremely slowly and with cooling to the hydrofluoric acid, resulting in an immediate and strongly exothermic reaction. The rate of solids addition was adjusted so that the temperature of the reacting solution remained below about 40° C. At the end of the addition the bright green slurry was allowed to stand with agitation for approximately one hour, and was then placed in an oven at 100° C. and dried to a cake. The cake was then ground, passed through a forty mesh sieve, mixed with 2% 425 mesh graphite and formed into 3/16 inch by 3/16 inch cylindrical pellets. The pellets were added to a tubular reactor and heated quickly to 500° C. with an electric furnace. Air preheated to the same temperature was passed over the pellets at approximately 2 liters per minute for a period of sixteen hours.

A control catalyst prepared in accordance with Ruh et al. (1961) was prepared as follows:

A reaction vessel equipped with stirrer and thermometer were immersed in an ice bath. To the vessel were added 84 parts by weight of 52% aqueous hydrofluoric acid and 156 parts by weight of distilled water. In a separate container 544 parts by weight of hydrated chromium fluoride were mixed with 136 parts by weight of aluminum fluoride and 20 parts by weight of sugar (sucrose). The agitator in the beaker containing the hydrofluoric acid was started and the mixture of solids was slowly added with no apparent chemical reaction. During the addition of solids, it was necessary to add an additional 175 parts by weight of distilled water in order to keep the slurry thin enough to agitate. After all of the solids had been added, the slurry was allowed to stand with the agitator turning for approximately two hours. At the end of that time the beaker and its contents were placed in an oven, dried, pelleted and activated with air as above.

An experimental apparatus was constructed to allow the catalyst pellets prepared by the methods described above to be continuously contacted with hydrogen fluoride and 1,1,1,3-tetrachloropropane vapors at 300° C. The catalyst was contained in a tubular reactor approximately one centimeter in inside diameter and 25 centimeters in length, which was also maintained at 300 degrees by an electric furnace. The gases exiting the reactor were passed successively through a trap, a flask containing 45% potassium hydroxide, a water-cooled condenser, a second flask of 45% potassium hydroxide, a tube filled with anhydrous calcium sulfate, a ball and tube type flowmeter previously calibrated for 3,3,3-trifluoropropene, a small chamber equipped with a septum through which a gas sample could be withdrawn for analysis and a refrigerant-cooled condenser operating at −60° C. Using this system the steady state performance of the catalyst could be monitored over extended periods of time by measuring the quantity and composition of the gases passing through the caustic solution. The gas composition was determined by injecting a 500 microliter sample of the uncondensed gas into a gas chromatograph equipped with 18 foot 20% SE-30 columns and thermal conductivity detectors.

To test the catalysts' performance, 12 grams (14.5 ml) of the control catalyst pellets (not in accord with this invention) were added to the tubular reactor and heated to 300° C. with nitrogen flowing through the reaction system. The flow of nitrogen was then stopped and a flow of hydrogen fluoride introduced in order to purge inert gases from the system. The flow of hydrogen fluoride was set at 2000 standard cubic centimeters (81.80 millimoles) per minute and, with the temperature still maintained at 300 degrees, a vaporized stream of 1.24 grams (6.81 millimoles) per minute of 1,1,1,3-tetrachloropropane was mixed with the hydrogen fluoride feed to the reactor. Thus, the molar feed ratio of hydrogen fluoride to 1,1,1,3-tetrachloropropane was 12.0, the total gas flow through the reactor was 88.61 millimoles per minute (4166 actual cubic centimeters per minute at the reaction temperature), and the contact time as calculated from the superficial velocity was 0.2 seconds.

The gas exiting the reactor was sampled once every hour after the start of the tetrachloropropane feed.

The above procedure was repeated, except that the tubular reactor of the system described above was filled with 12 grams (13 ml) of the catalyst prepared in accord with this invention. The apparatus was otherwise operated in exactly the same way. In this case the gas throughput and molar feed ratio of hydrogen fluoride to tetrachloropropane were the same as above, but the contact time was slightly less, being 0.18 seconds rather than 0.2 seconds.

The gas exiting the reactor was sampled once every hour after the start of the tetrachloropropane feed.

The following results were obtained:

| Catalyst | Control | This Invention |
|---|---|---|
| Temperature (°C.) | 300 | 300 |
| Feed Ratio | 12/1 | 12/1 |
| Contact Time (Sec) | 0.20 | 0.18 |
| Catalyst Age (g TCP* fed per g catalyst) | 3,3,3-$C_3H_3F_3$ Yield | 3,3,3-$C_3H_3F_3$ Yield |
| 6 | 84.6% | 94.8% |
| 12 | 66.3 | 93.1 |

*TCP = 1,1,1,3-tetrachloropropane

EXAMPLE 2

A fluorination was conducted exactly as in Example 1, except that the organic feed to the reaction system consisted of 95 weight percent 1,1,1,3-tetrachloropropane and 5 weight percent hexachloroethane instead of 100 percent 1,1,1,3-tetrachloropropane. The catalyst used was the control, not prepared according to this invention.

Another fluorination was conducted exactly as described above, except that the organic feed to the reaction system consisted of 95 weight percent, 1,1,1,3-tetrachloropropane and 5 weight percent hexachloroethane instead of 100 percent 1,1,1,3-tetrachloropropane. The catalyst used was prepared in accord with this invention.

The following results were obtained:

| Catalyst | Control | | This Invention | |
|---|---|---|---|---|
| Promoter | 5% $C_2Cl_6$ | | 5% $C_2Cl_6$ | |
| Temperature (°C.) | 300 | | 300 | |
| Feed Ratio | 12/1 | | 12/1 | |
| Contact Time (Sec) | 0.20 | | 0.20 | |
| Catalyst Age (g TCP fed/g ctlyst) | $C_3H_4Cl_4$ Conversion | 3,3,3-$C_3H_3F_3$ Yield | $C_3H_4Cl_4$ Conversion | 3,3,3-$C_3H_3F_3$ Yield |
| 6 | 94.5% | 53% | 95.4% | ~100% |
| 12 | 93.0 | 53 | 95.4 | ~100 |
| 19 | 90.1 | 53 | 95.2 | 86 |
| 31 | 82.9 | 47 | 95.2 | 74 |
| 62 | 72.8 | 26 | 91.4 | 72 |

EXAMPLE 3

A series of trials (A-E) was devised to show the effect of introducing chlorine gas to the fluorination of 1,1,1,3-tetrachloropropane:

Trial A 12 grams (13 ml) of catalyst pellets were added to the tubular reactor and heated to 300° C. with nitrogen flowing through the reaction system. The flow of nitrogen was then stopped and a flow of hydrogen fluoride introduced in order to purge inert gases from the system. The flow of hydrogen fluoride was set at 2000 standard cubic centimeters (81.80 millimoles) per minute and, with the temperature still maintained at 300 degrees, a vaporized stream of 2.0 grams (10.99 millimoles) per minute of 1,1,1,3-tetrachloropropane was mixed with the hydrogen fluoride feed to the reactor.

Thus, the molar feed ratio of hydrogen fluoride to 1,1,1,3-tetrachloropropane was 7.4, the total gas flow through the reactor was 92.79 millimoles per minute (4362 actual cubic centimeters per minute at the reaction temperature), and the contact time as calculated from the superficial gas velocity was 0.18 seconds.

The gas exiting the reactor was sampled once every hour after the start of the 1,1,1,3-tetrachloropropane feed.

Trial B

The tubular reactor of the system described in Trial A was filled with the same quantity of chromium oxyfluoride catalyst and the reaction system was started up in the same way. After reaching the desired temperature of 300 degrees, the flow rate of hydrogen fluoride was again adjusted to 2000 standard cubic centimeters (81.80 millimoles) per minute, but this time the addition rate of vaporized 1,1,1,3-tetrachloropropane was 1.24 grams (6.81 millimoles) per minute. The molar feed ratio of hydrogen fluoride to 1,1,1,3-tetrachloropropane was 12.0, the total gas flow through the reactor was 88.61 millimoles per minute (4166 actual cubic centimeters per minute at the reaction temperature), and the contact time as calculated from the superficial gas velocity was 0.2 seconds.

The gas exiting the reactor was sampled once every hour after the start of the 1,1,1,3-tetrachloropropane feed.

Trial C

The reaction system was charged with fresh catalyst and operated exactly as in Trial B, except that in this case the organic feed mixture consisted of 95 weight percent 1,1,1,3-tetrachloropropane and 5 weight percent hexachloroethane, instead of 100 percent 1,1,1,3-tetrachloropropane.

The gas exiting the reactor was sampled and analyzed every hour as in Trial B.

Trial D

Trial D was conducted exactly as Trial C except that the reaction temperature was maintained at 400° C. instead of 300° C.

Trial E

The reaction system used in the above trials was modified to allow a continuous addition of chlorine gas to the reactor feed, and the tubular reactor was charged with 6.6 grams (7 ml) of chromium oxyfluoride catalyst. The system was then started up and operated exactly as in Trial B, except that when the feed of 1,1,1,3-tetrachloropropane was started a continuous flow of chlorine was also introduced at a rate of 3 cubic centimeters (0.12 millimoles) per minute, so that the feed rate of chlorine was about 1.8 percent of the feed rate of 1,1,1,3-tetrachloropropane. Thus, the molar feed ratio of hydrogen fluoride to 1,1,1,3-tetrachloropropane was 12.0, the total gas flow through the reactor was 88.73 millimoles per minute (4172 actual cubic centimeters per minute at the reaction temperature), and the contact time as calculated from the superficial gas velocity was 0.10 seconds.

The gas exiting the reactor was sampled as described above once every hour after the start of the 1,1,1,3-tetrachloropropane and chlorine feeds.

The following results were observed:

| Trial | A | | B | | C | | D | | E | |
|---|---|---|---|---|---|---|---|---|---|---|
| Promoter | none | | none | | 5% $C_2Cl_6$ | | 5% $C_2Cl_6$ | | 2% $Cl_2$ | |
| Temperature (°C.) | 300 | | 300 | | 300 | | 400 | | 300 | |
| Feed Ratio | 7.4/1 | | 12/1 | | 12/1 | | 12/1 | | 12/1 | |
| Contact Time (Sec) | 0.18 | | 0.20 | | 0.20 | | 0.20 | | 0.10 | |
| Catalyst Age (g ICP fed per g Catalyst) | $C_3H_4Cl_4$ Conversion | 3,3,3-$C_3H_3F_3$ Yield | $C_3H_4Cl_4$ Conversion | 3,3,3-$C_3H_3F_3$ Yield | $C_3H_4Cl_4$ Conversion | 3,3,3-$C_3H_3F_3$ Yield | $C_3H_4Cl_4$ Conversion | 3,3,3-$C_3H_3F_3$ Yield | Conversion | 3,3,3-$C_3H_3F_3$ Yield |
| 6 | 13% | 92.5% | 11% | 94.8% | ~100% | 95.4 | ~100% | 95.4 | ~100% | — |
| 12 | 3 | 88.4 | 4 | 93.1 | ~100 | 95.4 | ~100 | 98.1 | ~100 | 98.3% |
| 19 | 1 | 82.3 | | | 86 | 95.2 | ~100 | 97.5 | ~100 | 97.6 |
| 31 | | | | | 74 | 92.2 | ~100 | 97.7 | ~100 | 96.7 |
| 62 | | | | | 72 | 91.4 | ~100 | 97.0 | ~100 | 96.1 |
| 93 | | | | | 61 | 87.8 | ~100 | 97.8 | ~100 | 99.0 |
| 124 | | | | | | | ~100 | 94.4 | ~100 | 99.3 |
| 155 | | | | | | | ~100 | 97.7 | ~100 | 99.2 |
| 186 | | | | | | | ~100 | 97.3 | ~100 | 99.4 |
| 217 | | | | | | | ~100 | 96.4 | ~100 | 99.3 |
| 248 | | | | | | | ~100 | 95.2 | ~100 | 99.4 |

EXAMPLE 4

Trial F

The reaction system was charged with fresh catalyst and operated exactly as in Trial B above, except that in this case the organic feed mixture consisted of 95 weight percent 1,1,1,3-tetrachloropropane and 5 weight percent pentachloroethane, instead of 100 percent 1,1,1,3-tetrachloropropane.

The gas exiting the reactor was sampled and analyzed every hour.

The following results were observed:

| Trial | A | | B | | C | | F | |
|---|---|---|---|---|---|---|---|---|
| Promoter | none | | none | | 5% $C_2Cl_6$ | | 5% $C_2HCl_5$ | |
| Temperature (°C.) | 300 | | 300 | | 300 | | 300 | |
| Feed Ratio | 7.4/1 | | 12/1 | | 12/1 | | 12/1 | |
| Contact Time (Sec) | 0.18 | | 0.20 | | 0.20 | | 0.20 | |
| Catalyst Age (g TCP fed per g catalyst) | $C_3H_4Cl_4$ Conversion | 3,3,3-$C_3H_3F_3$ Yield | $C_3H_4Cl_4$ Conversion | 3,3,3-$C_3H_3F_3$ Yield | $C_3H_3Cl_4$ Conversion | 3,3,3-$C_3H_3F_3$ Yield | $C_3H_4Cl_4$ Conversion | 3,3,3-$C_3H_3F_3$ Yield |
| 6 | 13% | 92.5% | 11% | 94.8% | ~100% | 95.4% | 91% | 97.2% |
| 12 | 3 | 88.4 | 4 | 93.1 | ~100 | 95.4 | 85 | 95.1 |
| 19 | 1 | 82.3 | | | 86 | 95.2 | 72 | 94.1 |
| 31 | | | | | 74 | 92.2 | 64 | 92.1 |
| 62 | | | | | 72 | 91.4 | 46 | 88.7 |
| 93 | | | | | 61 | 87.8 | 11 | 87.6 |

Obviously, many variations will suggest themselves to those skilled in this art in light of the above, detailed description. All such modifications are within the intended scope of the appended claims.

We claim:

1. A catalyst composition for promoting fluorination of a halogenated hydrocarbon by vapor-phase reaction with hydrogen fluoride comprising a chromium oxyfluoride compound prepared by simultaneous fluorination of an intimate admixture of chromium trioxide and alumina and activated by contact with an activating agent selected from the group consisting essentially of chlorine and pentachloroethane.

2. A catalyst as defined in claim 1, wherein said activating agent is chlorine.

3. A catalyst as defined in claim 1, wherein said activating agent is pentachloroethane.

4. A method for preparing a solid catalyst composition useful for promoting fluorination of a halogenated hydrocarbon by vapor-phase reaction with hydrogen fluoride comprising admixing a major proportion of chromium trioxide and a minor proportion of alumina; adding the admixture to aqueous hydrofluoric acid; drying the reaction product; and exposing the dried product to oxygen at a temperature of 350° C.–750° C.

5. A method as defined in claim 4 which further comprises activating said product by contacting it with an activating agent selected from the group consisting essentially of chlorine and pentachloroethane.

6. A method as defined in claim 4 which further comprises promoting said catalyst by contacting it with a chlorinated organic compound.

7. A method as defined in claim 6, wherein the chlorinated organic compound is 1,1-dichloroethane.

8. A method as defined in claim 6, wherein the chlorinated organic compound is hexachloroethane.

* * * * *